United States Patent
Zhang

(10) Patent No.: US 6,664,096 B2
(45) Date of Patent: Dec. 16, 2003

(54) METHODS FOR IMPROVED DIAGNOSIS AND TREATMENT OF MYCOBACTERIAL INFECTIONS

(76) Inventor: Ying Zhang, 2800 Millers Way Dr., Ellicott City, MD (US) 21043

( * ) Notice: Subject to any disclaimer, the term of this patent is extended or adjusted under 35 U.S.C. 154(b) by 8 days.

(21) Appl. No.: 10/005,920

(22) Filed: Dec. 7, 2001

(65) Prior Publication Data

US 2002/0127700 A1 Sep. 12, 2002

Related U.S. Application Data

(60) Provisional application No. 60/294,602, filed on Jun. 1, 2001, and provisional application No. 60/251,785, filed on Dec. 8, 2000.

(51) Int. Cl.⁷ .......................... C12N 1/00; A61K 39/00; A61K 39/02; A61K 39/04
(52) U.S. Cl. .................. 435/243; 424/9.1; 424/9.2; 424/184.1; 424/185.1; 424/190.1; 424/234.1; 424/248.1; 435/41; 435/252.1; 435/253.1; 435/863; 530/300; 530/350
(58) Field of Search ................. 424/9.1, 9.2, 184.1, 424/185.1, 190.1, 234.1, 248.1; 435/41, 243, 252.1, 253.1, 863; 530/300, 350

(56) References Cited

U.S. PATENT DOCUMENTS 4,769,332 A  *  9/1988  Siddiqi et al. .............. 435/244

OTHER PUBLICATIONS

Sun, Z., et al., "Spent culture supernatant of Mycobacterium tuberculosis H37Ra improves viability of aged cultures of this strain and allows small inocula to initiate growth", Journal of Bacteriology, pp. 7626–7628, Dec. 1999.*

* cited by examiner

Primary Examiner—Rodney P Swartz
(74) Attorney, Agent, or Firm—Whitham, Curtis & Christofferson, P.C.

(57) ABSTRACT

Media for growth enhancement and resuscitation of mycobacteria (such as *Mycobacterium tuberculosis, Mycobacterium paratuberculosis*, and *Mycobacterium leprae*) are provided. The media comprise isolated cell extract, early-stationary-phase or stationary phase supernatant, or a substantially purified component thereof such as a protein, a peptide fragment of the protein, or a phospholipid. The protein is Rv1147c and the phospholipid or a component of a phospholipid. Diagnostic methods and kits utilizing the media are also provided, as well as treatment methods utilizing spent culture supernatant and cell extracts, or components thereof.

57 Claims, No Drawings

METHODS FOR IMPROVED DIAGNOSIS AND TREATMENT OF MYCOBACTERIAL INFECTIONS

The present application claims priority to U.S. Provisional Application No. 60/294,602, filed Jun. 1, 2001, and U.S. Provisional Application No. 60/251,785, filed Dec. 8, 2000, herein each incorporated by reference in their entirety.

This invention was made using funds from the National Institutes of Health having grant number AI40584. The government may have certain rights in this invention.

BACKGROUND OF THE INVENTION

1. Field of the Invention

The invention generally relates to improved diagnosis and treatment of mycobacterial infections. In particular, the invention provides methods for using spent culture supernatant, components of the spent culture supernatant, or cell extracts to enhance cultivation of mycobacteria, or to revive dormant mycobacteria bacilli.

2. Background of the Invention

Tuberculosis (TB) is a leading infectious killer worldwide with 8 million new cases and 2 million deaths a year (WHO Report on the Tuberculosis Epidemic, 2000). One third of the world population is latently infected with *Mycobacterium tuberculosis*. The success of *M. tuberculosis* as a human pathogen relates to its remarkable ability to persist for long periods of time in the face of immunity and chemotherapy.

The current TB treatment is suboptimal, requiring a minimum of 6 months using the WHO recommended treatment regimen (DOTS, Directly Observed Treatment, Shortcourse), which consists of 4 drugs isoniazid, rifampin, pyrazinamide and ethambutol used in combination (WHO Report on the Tuberculosis Epidemic, 2000). Such lengthy treatments are expensive, and are likely to be problematic in terms of patient compliance. In addition, one potentially catastrophic effect of the lengthy therapy is the development of drug-resistant TB.

This lengthy treatment is thought to be due to the presence of a population of dormant bacilli in vivo that are not effectively killed by current TB drugs (McKinney et al., 1998). Dormant bacilli can be demonstrated in the Cornell mouse model of dormancy (McCune et al, 1966), where mice infected with tubercle bacilli were treated with INH and PZA for 2 months, at which time no viable bacilli were demonstrable in the tissues as judged by colony forming units (CFU); yet disease relapsed with viable yet drug susceptible bacilli after cessation of treatment for 3 months in one third of mice or in almost all mice given immunosuppressing steroids. This suggests that the drugs are unable to eliminate dormant bacilli completely and that although the dormant bacilli do not form colonies on plates they are not dead and can revive and cause disease when the immune system is compromised.

The unresponsiveness of dormant or nongrowing bacilli to DOTS is phenotypic or physiologic but not genetic, so that when the dormant bacilli revive and start growing they become susceptible to TB drugs again. Therefore, agents that cause dormant bacilli to revive and resuscitate so that they respond to treatment are potential modulators of drug activity in the host and can be used for improved treatment of the disease by potentially shortening the treatment time.

The current diagnosis of tuberculosis still relies on culture of the *M. tuberculosis* organism as the definitive method of diagnosis. However, *M. tuberculosis* grows very slowly and it takes several weeks for the primary isolation of the bacilli from clinical specimens for confirmation of the disease. Current clinical diagnosis uses solid media such as Lowenstein-Jensen medium, 7H10 or 7H11 agar medium and liquid 7H12B medium as in BACTEC460 machine for primary isolation of the bacilli from clinical specimen. In general, the liquid 7H12B based medium is more sensitive in terms of primary isolation of positive cultures from clinical specimens. However, the current medium for isolation of *M. tuberculosis* from clinical specimens is not optimal. Even with liquid 7H12B medium in the presence of growth enhancing agent POES (polyoxyethelene stearate) (Becton Dickinson, Sparks, Md., U.S. Pat. No. 4,769,332), the isolation rate is about 80%, and some 20% samples which later prove to be containing the bacilli are not easily detected. Agents that can improve the primary isolation sensitivity and enhance the growth of *M. tuberculosis* should improve the ability to diagnose TB.

SUMMARY OF THE INVENTION

The present invention provides media and methods for enhancing the cultivation of mycobacteria, or reviving (resuscitating) dormant bacilli from mycobacterium species. The media and methods utilize mycobacterial products from the *M. tuberculosis* complex. By "*M. tuberculosis* complex" we mean *M. tuberculosis* complex organisms which include *M. tuberculosis*, *Mycobacterium bovis*, including the vaccine strain BCG, and *Microbacterium microti*. The products include cell extracts, early-stationary-phase culture supernatant (ESPSN), and stationary phase culture supernatant (SPSN), either crude or as substantially purified components from these sources. The products may be used to enhance the growth of mycobacterial species that are difficult to culture, and/or to effect the resuscitation of dormant mycobacteria bacilli.

It is an object of this invention to provide a supplemented medium for culturing mycobacterium species, for example *Mycobacterium tuberculosis*, *Mycobacterium paratuberculosis*, and *Mycobacterium leprae*. The medium comprises a cell extract from *M. tuberculosis* complex, or at least one product from *M. tuberculosis* complex (e.g. a component of early-stationary-phase culture supernatant (ESPSN), of stationary phase culture supernatant (SPSN), or of a cell extract) and a suitable culture medium. The cell extract or substantially purified product exhibits resuscitation activity for dormant bacilli of the mycobacterium species, or the ability to enhance the growth of the mycobacterium species. The substantially purified product may be a phospholipid or a component of a phospholipid, such as phosphotidyl-L-serine, dioleoyl phosphotidyl-L-serine, phosphotidylcholine, phosphotidylethanolamine, tuberculostearic acid, arachidonic acid, and fatty acids. Alternatively, the substantially purified product may be a protein or a fragment of a protein, e.g. protein Rv1147c (accession number F70875 in the National Institute of Health's Entrez Protein Database), a peptide corresponding to SEQ ID NO. 1, a peptide corresponding to SEQ ID NO. 2, a peptide corresponding to SEQ ID NO. 3, a peptide corresponding to SEQ ID NO. 4 and a peptide corresponding to SEQ ID NO. 5. Suitable culture media to be supplemented include 7H12B, 7H9, 7H10, 7H11, Sauton's medium, Dubos medium, and egg-based media (for example Lowenstein-Jensen medium). In addition, a mixture of substantially purified component of ESPSN or SPSN may be utilized, e.g. a mixture of phospholipids and/or proteins and peptides.

In addition, isolated and sterilized ESPSN or SPSN of *M. tuberculosis* complex can itself be utilized as a culture medium, or combined with a suitable fresh culture medium or other fresh nutrients to produce supplemented culture medium. Further, substantially purified components of ESPSN, SPSN, or mycobacterium cell extracts that exhibit resuscitation activity for dormant bacilli of the mycobacterium species may be added.

In another aspect, the present invention provides a method for reviving dormant mycobacterium bacilli of, for example *Mycobacterium tuberculosis, Mycobacterium paratuberculosis,* and *Mycobacterium leprae*. According to the method, dormant bacilli are exposed to a cell extract or at least one substantially purified product of *M. tuberculosis* complex (e.g. a component of early-stationary-phase culture supernatant (ESPSN), of stationary phase culture supernatant (SPSN), or of a cell extract). The cell extract and substantially purified product exhibit resuscitation activity for dormant bacilli of the mycobacterium species, and the cell extract or product is present in sufficient quantity to effect revival of the dormant bacilli. The substantially purified product may be a phospholipid or component thereof, e.g. phosphotidyl-L-serine, dioleoyl phosphotidyl-L-serine, phosphotidylcholine, or phosphotidylethanolamine, tuberculostearic acid, arachidonic acid, and fatty acids. Alternatively, the substantially purified product may be a protein or a fragment of a protein, e.g., protein Rv1147c, a peptide corresponding to SEQ ID NO. 1, a peptide corresponding to SEQ ID NO. 2, a peptide corresponding to SEQ ID NO. 3, a peptide corresponding to SEQ ID NO. 4 and a peptide corresponding to SEQ ID NO. 5. In addition, a mixture of substantially purified products may be utilized, e.g. a mixture of phospholipids and/or proteins and peptides.

In addition, dormant bacilli may be revived by exposure to cell extract or isolated and sterilized ESPSN or SPSN of *M. tuberculosis* complex, which may also be combined with a suitable fresh culture medium or other fresh nutrients (e.g. substantially purified components of ESPSN, SPSN, or mycobacterium cell extracts that exhibit resuscitation activity for dormant bacilli).

In yet another aspect of the present invention, a method for the diagnosis of an infection caused by a mycobacterium species (for example *Mycobacterium tuberculosis, Mycobacterium paratuberculosis,* and *Mycobacterium leprae*) is provided. The method comprises combining a sample for which the presence or absence of the mycobacterium species is to be determined with medium supplemented with cell extract or at least one substantially purified product *M. tuberculosis* complex (e.g. a component of early-stationary-phase culture supernatant (ESPSN), of stationary phase culture supernatant (SPSN), or of a cell extract); and analyzing the culture for the presence of the mycobacterium species. The cell extract and substantially purified product exhibits growth enhancement and/or resuscitation activity for dormant bacilli of the mycobacterium species. If the mycobacterium species is found in the culture, this indicates a positive diagnosis for the infection. The substantially purified product may be a phospholipid or component of a phospholipid, e.g. phosphotidyl-L-serine, dioleoyl phosphotidyl-L-serine, phosphotidylcholine, or phosphotidylethanolamine, tuberculostearic acid, arachidonic acid, and fatty acids. Alternatively, the substantially purified product may be a protein or a fragment of a protein, e.g. protein Rv1147c, a peptide corresponding to SEQ ID NO. 1, a peptide corresponding to SEQ ID NO. 2, a peptide corresponding to SEQ ID NO. 3, a peptide corresponding to SEQ ID NO. 4 and a peptide corresponding to SEQ ID NO. 5. In addition, a mixture of substantially purified products may be utilized, e.g. a mixture of phospholipids and/or proteins and peptides.

In addition, the method for the diagnosis of an infection caused by a mycobacterium species may comprise combining a sample for which the presence or absence of the mycobacterium species is to be determined with isolated and sterilized ESPSN or SPSN of *M. tuberculosis* complex, which may also be combined with a suitable fresh culture medium or other fresh nutrients (e.g. substantially purified components of ESPSN, SPSN, or mycobacterium cell extracts that growth enhancing or resuscitation activity for dormant bacilli).

In another aspect of the present invention, a kit for the diagnosis of an infection caused by a mycobacterium species (for example *Mycobacterium tuberculosis, Mycobacterium paratuberculosis,* and *Mycobacterium leprae*) is provided. The kit includes a sealed container of medium supplemented with cell extract or at least one substantially purified product of *M. tuberculosis* complex (e.g. a component of early-stationary-phase culture supernatant (ESPSN), of stationary phase culture supernatant (SPSN), or of a cell extract), which may further comprise additional fresh media or nutrients. The cell extract or substantially purified product exhibits growth enhancement and/or resuscitation activity for dormant bacilli of the mycobacterium species. The substantially purified product may be a phospholipid or a component of a phospholipid e.g. phosphotidyl-L-serine, dioleoyl phosphotidyl-L-serine, phosphotidylcholine, or phosphotidylethanolamine, tuberculostearic acid, arachidonic acid, and fatty acids. Alternatively, the substantially purified product may be a protein or a fragment of a protein, e.g. protein Rv1147c, a peptide corresponding to SEQ ID NO. 1, a peptide corresponding to SEQ ID NO. 2, a peptide corresponding to SEQ ID NO. 3, a peptide corresponding to SEQ ID NO. 4 and a peptide corresponding to SEQ ID NO. 5. In addition, a mixture of substantially purified products may be utilized, e.g. a mixture of phospholipids and/or proteins and peptides.

In addition, the kit may comprise isolated and sterilized ESPSN or SPSN of *M. tuberculosis* complex, which may also be combined with a suitable fresh culture medium or other fresh nutrients (e.g. substantially purified components of ESPSN, SPSN, or mycobacterium cell extracts that exhibit growth enhancement or resuscitation activity for dormant bacilli).

The present invention further provides a method for the treatment of an infection caused by a mycobacterium species (for example *Mycobacterium tuberculosis, Mycobacterium paratuberculosis,* and *Mycobacterium leprae*). According to the method, cell extract or at least one substantially purified product of *M. tuberculosis* complex (e.g. a component of early-stationary-phase culture supernatant (ESPSN), of stationary phase culture supernatant (SPSN), or of a cell extract), is administered to said patient, in conjunction with drugs of an established treatment protocol for the infection in order to ameliorate symptoms associated with the infection. Administering such a substance results in the revival of dormant bacilli of the mycobacterium species in the patient, thus making the bacilli susceptible to treatment with an antibiotic. (Dormant bacilli are otherwise not susceptible to current drug therapy protocols.) The substantially purified product may be a phospholipid e.g. phosphotidyl-L-serine, dioleoyl phosphotidyl-L-serine, phosphotidylcholine, or phosphotidylethanolamine, tuberculostearic acid, arachidonic acid, and fatty acids. Alternatively, the substantially purified product may be a protein or a fragment of a protein, e.g. protein Rv1147c, a peptide corresponding to SEQ ID NO. 1, a peptide corresponding to SEQ ID NO. 2, a peptide corresponding to SEQ ID NO. 3, a peptide corresponding to SEQ ID NO. 4 and a peptide corresponding to SEQ ID NO. 5. In addition, a mixture of substantially purified products may be utilized, e.g. a mixture of phospholipids and/or proteins and peptides.

In another aspect, the present invention provides a pharmacological agent for the treatment of an infection caused by a mycobacterium species (for example *Mycobacterium tuberculosis, Mycobacterium paratuberculosis,* and *Mycobacterium leprae*). The agent comprises cell extract or at least one substantially purified product of *M. tuberculosis* complex (e.g. a component of early-stationary-phase culture supernatant (ESPSN), of stationary phase culture supernatant (SPSN), or of a cell extract). The substantially purified product may be a phospholipid, e.g. phosphotidyl-L-serine, dioleoyl phosphotidyl-L-serine, phosphotidylcholine, or phosphotidylethanolamine, tuberculostearic acid, arachidonic acid, and fatty acids. Alternatively, the substantially purified product may be a protein or a fragment of a protein, (for *Mycobacterium tuberculosis,* protein Rv1147c, a peptide corresponding to SEQ ID NO. 1, a peptide corresponding to SEQ ID NO. 2, a peptide corresponding to SEQ ID NO. 3, a peptide corresponding to SEQ ID NO. 4 and a peptide corresponding to SEQ ID NO. 5., and a physiologically suitable carrier. In addition, a mixture of substantially purified products may be utilized, e.g. a mixture of phospholipids and/or proteins and peptides.

DETAILED DESCRIPTION OF THE PREFERRED EMBODIMENTS OF THE INVENTION

The present invention provides media and methods for enhancing the cultivation of mycobacteria, or reviving (resuscitating) dormant bacilli from mycobacterium species. The media and methods utilize mycobacterial products from, for example, the early stationary phase supernatant (ESPSN), the stationary phase supernatant (SPSN), or cell extracts of cultures of mycobacterium. The products exhibit growth enhancement of mycobacteria, or resuscitation activity for dormant bacilli of mycobacterium species, examples of which include but are not limited to *Mycobacterium tuberculosis, Mycobacterium paratuberculosis,* and *Mycobacterium leprae*. By the "revival" or "resuscitation" of dormant bacilli, we mean that bacilli that do not display characteristics of growth (e.g. they do not form colonies on suitable media, or do not test as live with FDA-EB staining) obtain the ability to display growth-related characteristics, (e.g. the ability to form colonies on suitable media or to test as live with FDA-EB staining). By "enhancement of growth" we mean that the amount of growth exhibited by a mycobacterial culture is increased at least about two-fold compared to a control culture to which the supplement has not been added.

The invention is predicated on the novel finding that the early stationary phase supernatant (ESPSN) and the stationary phase supernatant (SPSN) of cultures of the mycobacterium have the ability to cause the revival or resuscitation of dormant bacilli, and to generally enhance the growth of mycobacterial cultures.

When a batch culture of bacteria grows to stationary phase, bacterial growth halts because of the exhaustion of essential nutrients and accumulation of toxic products (Postgate, 1967). Upon extended incubation in stationary phase, bacteria begin to die and viability of the culture decreases. The number of colony forming units (CFU) of an aged stationary batch culture is often orders of magnitude less than the total number of bacteria in the culture (Amann et al., 1995; Kaprelyants and Kell, 1993; Votyakova et al., 1994). The nonculturable bacterial population consists of dead cells as well as injured or dormant cells. The present invention capitalizes on the discovery that dormant *M. tuberculosis* cells can be induced to revive upon exposure to ESPSN or SPSN. Further, individual components of the ESPSN and SPSN that possess this ability have been identified and substantially purified. Several embodiments of this discovery are herein disclosed, namely media for culturing mycobacterium, methods for reviving dormant mycobacterium bacilli, improved methods for the diagnosis of infections caused by mycobacterium, kits for the diagnosis of infections caused by mycobacterium, improved methods for the treatment of infections caused by mycobacterium, and a pharmaceutical preparation for the treatment of infections caused by mycobacterium.

The present invention provides media for culturing a mycobacterium species comprising the isolated and sterilized ESPSN or SPSN of the mycobacterium species. In a preferred embodiment of the present invention, the mycobacterium species is *Mycobacterium tuberculosis* (*M. tuberculosis*). Those of skill in the art will recognize, however, that the compositions and methods disclosed herein are equally applicable to other mycobacterial species, including but not limited to *Mycobacterium paratuberculosis* (the causative agent of Crohn's disease in humans and Johne's disease in cattle), and *Mycobacterium leprae* (the causative agent of leprosy). Mycobacterial species have many commonalities, such as the difficulty of establishing them in culture. It is well known that to initiate the growth of *M. tuberculosis,* a large inocula are needed and small inocula often fail to initiate the growth. It is very likely that growth of *M. tuberculosis* requires autocrine factors secreted by adjacent bacilli for the small inocula to grow. Supplement of such factors from ESPSN or SPSN or cell extract containing the autocrine factors to the culture media can potentially allow small inocula to grow, which otherwise cannot grow. Thus this method of cultivation using ESPSN, or SPSN, or cell extract of *M. tuberculosis* complex organisms can be used to improve the sensitivity of isolation of *M. tuberculosis* complex from clinical specimens, and also for improved growth of the *M. tuberculosis* complex organisms for research lab use. Therefore, while the methodology described herein utilizes *M. tuberculosis* in many examples, one of skill in the art will recognize that it can readily be adapted to other mycobacterial species.

By ESPSN we mean the supernatant obtained from the early stationary phase of a culture, e.g. for *M. tuberculosis* complex a supernatant obtained from an approximately 3–4 week old culture. By SPSN we mean the supernatant obtained from the stationary phase, e.g. for *M. tuberculosis* complex from an approximately 1–2 month old culture. By "isolated and sterilized" we mean that the supernatant has been treated to remove particulate matter and sterilized to eliminate mycobacteria or other contaminating organisms. Collection of the supernatant, removal of particulate matter, and sterilization may be accomplished by any of a variety of means which are well known to those of skill in the art. For example, collection may be accomplished via centrifugation (e.g. about 6,000× g for about 20 minutes) followed by sterilization via filtration, e.g. through a 0.22 µm filter. Those of skill in the art will recognize that other suitable means of accomplishing collection and sterilization of the supernatant are available and well-known, including but not limited to centrifugation followed by UV irradiation.

As demonstrated herein, the isolated ESPSN and SPSN from *M. tuberculosis* complex contain factors which promote the revival or resuscitation of dormant mycobacterium bacilli. In order to be utilized for this purpose, the isolated ESPSN or SPSN may be used alone, or may be supplemented or enriched with various nutrients in order to enhance growth of a new inoculum. Those of skill in the art will recognize that media comprised of ESPSN or SPSN may be enriched by the addition of other substances known to be conducive to the growth of bacteria in general, and of mycobacterium in particular, for example, Tween 80, albumin-dextrose-catalase, various salts and nutrients, buffering agents, fatty acids and the like. Nutrients may be added individually to the ESPSN or SPSN. Alternatively, the ESPSN or SPSN may be combined with other fresh media to supply the nutrients.

In order to obtain ESPSN, SPSN or cell extracts, a culture of mycobacterium must be established. Methods of culturing mycobacterium are well-known to those of skill in the art (see, for example Kent, P T, Kubica, G P. Public health mycobacteriology. A guide for the level III laboratory. Atlanta, Ga.; Centers for Disease Control, 1985; Nolte, F S, Metchcock B. Mycobacterium. In: Murray P R, Baron E J, Pfaller M A, Tenowver F C, Yolken R H ed. Manual of clinical microbiology, 6th ed. Washington D.C.; ASM Press 1995: pp 400–437) as are methods of obtaining a suitable supernatant from such a culture. In general, an inoculum from an appropriate strain of mycobacterium is introduced into a culture medium and allowed to grow for the requisite period of time under conditions that are well-known to those of skill in the art (e.g. sterile conditions, about 37° C., with or without agitation of the culture). Suitable strains of mycobacterium which may be utilized in the practice of the present invention include but are not limited to $M.$ $tuberculosis$ H37Ra, $[M. fortuitum]$ $M. fortuitum,$ etc. Useful media for culturing $M.$ $tuberculosis$ strains include but are not limited to 7H9, 7H10, 7H11, 7H12B, Sauton's medium, Dubos medium, egg-based media such as Lowenstein-Jensen medium, and the like, which are readily commercially available (e.g. Difco). Further, those of skill in the art will recognize that such media may be supplemented with substances such as Tween 80 (0.05%), albumin-dextrose-catalase (ADC), fatty acids, and the like.

The inoculated cultures are grown under suitable conditions until early stationary phase (ESP) is achieved. Typically, for $M.$ $tuberculosis$ complex the culture will be grown for approximately 3–4 weeks, and the optical density of the culture at 600 nm will be in the range of about 1.0 to 1.5, and more preferably will be in the range of about 1.0 to 1.2. Alternatively, if SPSN is to be utilized, the culture is grown for about 1–2 months prior to obtaining the supernatant. The supernatant can then be isolated and sterilized as described above, and utilized to revive or resuscitate dormant bacilli.

By "revive or resuscitate dormant mycobacterium bacilli" and "enhance growth" we mean that a significant increase in the growth of a sample containing dormant bacilli is observed when the sample is cultured in the media of the present invention, compared to the growth of an equivalent sample cultured in conventional media. An equivalent sample would be one in which an equal amount of inoculum was introduced into an equal volume of media, and in which all other variables other than the presence/absence of isolated supernatant or components thereof, (e.g. temperature, degree of aeration, time of culturing, and the like) are held constant. By "increase in growth" we mean an increase in the total number of bacteria in the culture, as determined by any of several techniques that are well-known to those of skill in the art. Such techniques include ascertaining the number of colony forming units (CFUs) present in the culture after incubation for a fixed amount of time, or by ascertaining the number of bacteria which test live in an FDA-EB test. In a preferred embodiment of the present invention, the quantitation of growth in the conventional and the supplemented medium may be carried out after a suitable time. For example, the cultures should be incubated for a minimum of about 2 days and for a maximum of about 7 to 28 days. The determination of growth in a culture may be carried out by any of a variety of techniques that are well-known to those of skill in the art, including but not limited to plating on solid media and visually observing colony formation (i.e. determining CFUs), observing an increase in turbidity in liquid culture as measured by optical density at absorption A600, or by utilizing a viability assay with redox dye such as MTT (3-[4,5-dimethylthiazol-2-yl]-2,5-diphenyltetrazolium), or by detecting an increase in growth index (GI) value due to production of $C^{14}$—$CO_2$ in the Bactec TB460 system, and the like. The increase in growth that is observed, in order to be considered "significant" is preferably at least about a two fold increase in growth. Alternatively, what may be observed is the emergence of any growth at all compared to a control in which no growth is observed without the resuscitation factors. In yet another embodiment of the present invention, a media is provided which is prepared from ESPSN and/or SPSN combined with fresh, conventional media. Examples of suitable media include but are not limited to 7H9, 7H10, 7H11, 7H12B, Sauton's medium, Dubos medium, egg-based media such as Lowenstein-Jensen medium, and the like, which are readily commercially available (e.g. Difco). Further, those of skill in the art will recognize that such media may be enriched with suitable substances such as Tween 80, albumin-dextrose-catalase (ADC), fatty acids, and the like. The medium of the present invention may be prepared by combining ESPSN and/or SPSN with any suitable media, so long as the resulting medium appropriately sustains the growth of mycobacterium and supports the revival or resuscitation of dormant bacilli. Generally, the ratio of ESPSN and/or SPSN to media will be in the range of from about 0.1:1 to about 1:10, and more preferably in the range of from about 1:1 to about 1:2. Further, the media may also be further supplemented by the addition of substantially purified components of ESPSN and/or SPSN such as the proteins, peptides and phopholipids (or mixtures thereof) described below.

In another embodiment, the present invention further provides media for culturing mycobacterium which is comprised of a suitable culture medium supplemented with cell extract at least one substantially purified product of $M.$ $tuberculosis$ complex, the product exhibiting growth enhancing/resuscitation activity for dormant bacilli of the mycobacterium. Such products may be obtained from, for example, the ESPSN or the SPSN of a $M.$ $tuberculosis$ complex culture, or from cellular extracts of such a culture. While the examples recited herein disclose products from the ESPSN or the SPSN, those of skill in the art will recognize that those products are of cellular origin and are released into the supernatant from the bacteria. Thus, the products may also be obtained directly from cell extracts prior to their release from the cell. Alternatively, crude cell extracts may also be utilized. Methods of obtaining such extracts are well known to those of skill in the art and include but are not limited to sonication, French press, grinding with mortar and pestle, and the like. The amount of cell extract that can be added to fresh media to fabricate the supplemented media is in the range of about from 1:10 to about 1:1000, cell extract: media.

By "substantially purified product" we mean a product which has been purified to contain no more than about 0–20%, and more preferably about 0–10%, and even more preferably about 0–5% extraneous material. Those of skill in the art will recognize that substantially purified components may contain trace amounts of material such as salts, ions (e.g. metal ions), and various other extraneous materials that do not interfere with the resuscitation activity exhibited by the substantially purified components.

In a preferred embodiment of the present invention, the mycobacterium is $M.$ $tuberculosis$ and the component of ESPSN and/or SPSN or cell extract is the protein Rv1147c or a peptide fragment of protein Rv1147c. By "protein Rv1147c" we mean the protein corresponding to the amino acid sequence encoded by the open reading frame of the $M.$ $tuberculosis$ genome sequence which has been designated $M.$ $tuberculosis$ Rv1147c (accession number F70875 in the National Institute of Health's Entrez Protein Database).

Those of skill in the art will recognize that other amino acid sequences which are not absolutely identical to the sequence of protein Rv1147c may also be utilized in the practice of the present invention. For example, proteins with various amino acid substitutions, or with various deletions or insertions in the sequence (e.g. such as those that may occur in variants of $M.$ $tuberculosis$ or which are generated via genetic engineering, etc.), or with various chemical modifications (e.g. acylation of the carboxy terminus), may also be utilized, so long as they retain the ability to function in the practice of the present invention. In general, such Rv1147c-based proteins will possess high homology to Rv1147c, i.e. in the range of about 75 to 100% homology, or more preferably in the range of about 85 to 100% homology, and most preferably in the range of about 95–100% homology to Rv1147c. Further, the protein Rv1147c may be from any source (e.g. isolated from $M.$ $tuberculosis$, or from another organism into which the gene encoding the protein has been cloned, or fabricated synthetically, etc.)

Further, the component of ESPSN and/or SPSN or cell extract may be a peptide fragment of Rv1147c. Examples of such peptide fragments include but are not limited to those with the amino acid sequences of SEQ IDS NOS. 1–5 of the instant invention. However, those of skill in the art will recognize that many variations of these peptides may be made (for example, by varying the primary sequence of the peptides by amino acid substitutions, deletions or insertions, or by extending or shortening their length, etc.) and all such modified peptide fragments of Rv1147c are intended to be encompassed in the practice of the present invention. Any peptide fragment of Rv1147c may be utilized in the practice of the present invention, including peptides which are based on or are obvious variants of SEQ IDS 1–5. In general, the length of such a peptide fragment of Rv1147c will be from about 5 to about 20 amino acids. Further, the peptide fragments may be from any suitable source, e.g. they may be generated by chemical or proteolytic cleavage of Rv1147c or related proteins, they may be produced synthetically, or they may be produced via genetic engineering techniques. The particular source of the ESPSN and SPSN-based protein or peptides of the present invention is not a crucial feature of the invention.

The concentration of protein or peptide to be present in the media of the present invention may vary depending on the resuscitation activity of a given protein or peptide. However, it will generally be in about the picomolar to micromolar range. Typically, the concentration should be adequate to provide a significant increase in the CFU forming ability of dormant bacilli, compared to conventional, unsupplemented media.

In another embodiment of the present invention, the substantially purified component of ESPSN and/or SPSN or cell extract is a phospholipid or a component of a phospholipid. Phospholipids (also called phosphoglycerides) are composed of glycerol, phosphate and two fatty acyl units. Thus fatty acid components can have a carbon chain length of, for example, C18 (octadecanoic acid), C19 (nonadecanoic acid), 20 (eicosanoic acid), 21 (heneicosanoic acid), 22 (docosanoic acid), 23 (tricosanoic acid) 24 ((tetracosannoic acid), 25 (pentacosanoic acid), 26 (hexacosanoic acid), 27 (heptacosanoic acid), 28 (octacosanoic acid), 29 (nonacosanoic acid), 30 (triacontanoic acid), 31 (hentriacontanoic acid). Derivatives of these fatty acids, such as with double bonds and esters of these fatty acids can, either alone or in combination, be added to the culture media (7H12B, 7H9, 7H10, 7H11, Sauton's medium, Dubos medium and egg-based media such as Lowenstein-Jensen medium) for improved diagnosis and treatment of mycobacterial infections. In a preferred embodiment of the present invention, the phospholipid or component of a phospholipid is phosphotidyl-L-serine, dioleoyl phosphotidyl-L-serine, phosphotidylcholine, phosphotidylethanolamine, tuberculostearic acid, arachidonic acid, C18–C31 fatty acids with or without double bonds, and esters of C18–C31 fatty acids with or without double bonds. Such phospholipids are well-known to those of skill in the art and are readily available.

The concentration of phospholipid or component thereof to be present in the media of the present invention may vary depending on the resuscitation activity of a given phospholipid. However, it will generally be in about the picomolar to micromolar range. Typically, the concentration should be adequate to provide a significant increase in the CFU forming ability of dormant bacilli, compared to conventional, unsupplemented media.

In addition, the media of the present invention may comprise more than one substantially purified component of ESPSN and/or SPSN or cell extract. For example, a combination of several peptide fragments, or of several lipids, or of several peptides and several lipids may also be utilized. In this case, the concentration of each component will typically be in the picomolar to micromolar range.

Types of media that may be supplemented by components of ESPSN and/or SPSN or cell extract include but are not limited to 7H12B, 7H9, 7H10, 7H11, Sauton's medium, Dubos medium and egg-based media such as Lowenstein-Jensen medium. Further, those of skill in the art will recognize that the media of the present invention may be provided in any of several suitable forms. For example, the media may be provided in a premixed form (i.e. the components have already been added) or the components may be provided separately for addition to conventional media. Further, the media may be liquid (ready to use or concentrated) or solid.

The invention further provides methods for reviving dormant bacilli of a mycobacterium species. In one embodiment of the present invention, the method involves exposing dormant bacilli to isolated ESPSN or SPSN from $M.$ $tuberculosis$ complex cultures. The isolated ESPSN and SPSN will preferably have been sterilized, e.g. by filter sterilization.

In another embodiment of the present invention, the revival method involves exposing dormant bacilli of a mycobacterium species to a cell extract or at least one substantially purified product of $M.$ $tuberculosis$ complex (e.g. from the ESPSN, the SPSN, or a cell extract), the product exhibiting resuscitation activity for dormant bacilli of mycobacterium. In one embodiment, the product is a phospholipid or component thereof. In a preferred embodiment of the present invention, the phospholipid is phosphotidyl-L-serine, dioleoyl phosphotidyl-L-serine, phosphotidylcholine, phosphotidylethanolamine, tuberculostearic acid, arachidonic acid, or a fatty acid. In another embodiment, the product is a protein. In a preferred embodiment of the present invention the protein is Rv1147c or a peptide fragment of protein Rv1147c. Exemplary peptide fragments of Rv1147c include the peptides corresponding to SEQ ID NOS. 1–5.

Methods for the diagnosis of infections caused by a mycobacterium species (such as *Mycobacterium tuberculosis, Mycobacterium paratuberculosis*, and *Mycobacterium leprae*) are also contemplated. Improved methods are needed because, in the case of, for example, tuberculosis (caused by an *M. tuberculosis* infection), clinical specimens from suspected TB patients, especially those from patients under treatment, are known to contain injured and dormant bacilli, which may not grow in conventional culture media. In addition, bacilli in the specimens will also suffer from significant stress and injury during the processing of the clinical specimens by strong alkali NaOH and the centrifugation heat. Addition of the growth enhancing/resuscitation factors is likely to resuscitate the dormant or injured bacilli in the clinical specimens, resulting in a better recovery rate or improved sensitivity of primary isolation or the bacilli. The diagnostic methods of the instant invention are geared to detecting live and/or dormant *M. tuberculosis* bacilli with a far greater level of confidence. The diagnostic methods of the present invention may be used, for example, to screen persons suspected of having tuberculosis, or to monitor the progress of eradication of *M. tuberculosis* bacilli during or after treatment. In whatever context the diagnostic method is used, it would be highly advantageous to have the ability to detect dormant or injured forms of bacilli.

In one embodiment, the diagnostic method involves combining a sample for which the presence or absence of a mycobacterium species is to be ascertained with isolated early stationary phase supernatant of *M. tuberculosis* complex. The isolated ESPSN may have been sterilized e.g. by filter sterilization.

In another embodiment of the present invention, the diagnostic method involves combining a sample for which the presence or absence of a mycobacterium species is to be ascertained with a cell extract or at least one substantially purified product of *M. tuberculosis* complex (e.g. a component of ESPSN and/or SPSN culture supernatant or of a cell extract of the mycobacterium species). The cell extract or product exhibit the property of enhancing the growth of or resuscitating dormant bacilli of mycobacteria. In one embodiment, the product is a phospholipid or component of a phospholipid. In a preferred embodiment, the phospholipid or component thereof is, for example, phosphotidyl-L-serine, dioleoyl phosphotidyl-L-serine, phosphotidylcholine, phosphotidylethanolamine, tuberculostearic acid, arachidonic acid, or a fatty acid. In another embodiment, the product is the protein Rv1147c or a peptide fragment of protein Rv1147c. Exemplary peptide fragments of Rv1147c include the peptides corresponding to SEQ ID NOS. 1–5. Further, the method may also utilize combinations of such products.

Suitable samples for analysis by the methods of the present invention include but are not limited to sputum, blood, tissue, and the like.

The present invention also provides a kit for use in the diagnosis of infections caused by a mycobacterium species (such as *Mycobacterium tuberculosis, Mycobacterium paratuberculosis*, and *Mycobacterium leprae*. In one embodiment, the kit comprises a sealed container comprising isolated ESPSN and/or SPSN of *M. tuberculosis* complex. The isolated supernatant may have been sterilized e.g. by filter sterilization. In another embodiment of the invention, the kit comprises a sealed container comprising cell extract or at least one substantially purified product of *M. tuberculosis* complex, the product displaying the property of resuscitating dormant bacilli of mycobacteria, or generally enhancing the growth of the mycobacteria. In preferred embodiments, the product is a component of ESPSN, SPSN, or a cell extract of *M. tuberculosis* complex. In one embodiment, the component is a phospholipid or component of a phospholipid. In a preferred embodiment, the phospholipid or component thereof is, for example, phosphotidyl-L-serine, dioleoyl phosphotidyl-L-serine, phosphotidylcholine, phosphotidylethanolamine, tuberculostearic acid, arachidonic acid, or a fatty acid. In another embodiment, the product is a protein. In a preferred embodiment of the present invention, the protein Rv1147c or a peptide fragment of protein Rv1147c. Exemplary peptide fragments of Rv1147c include the peptides corresponding to SEQ ID NOS. 1–5. Further, the kit may also comprise combinations of such products, as well as such items as instructions for use of the kit.

Another aspect of the present invention is the treatment of infections caused by a mycobacterium species (such as *Mycobacterium tuberculosis, Mycobacterium paratuberculosis,* and *Mycobacterium leprae*). The treatment method involves the administration to a patient cell extract or at least one substantially purified product of *M. tuberculosis* complex, the product or extract displaying the property of resuscitating dormant bacilli of mycobacteria, or generally enhancing the growth of mycobacteria. In preferred embodiments, the product is a component of ESPSN, SPSN, or a cell extract of *M. tuberculosis* complex. In one embodiment, the component is a phospholipid or component of a phospholipid. In a preferred embodiment, the phospholipid or component is, for example, phosphotidyl-L-serine, dioleoyl phosphotidyl-L-serine, phosphotidylcholine, phosphotidylethanolamine, tuberculostearic acid, arachidonic acid, or a fatty acid. In another embodiment, the product is a protein. In a preferred embodiment of the present invention, the protein is Rv1147c or a peptide fragment of protein Rv1147c. Exemplary peptide fragments of Rv1147c include the peptides corresponding to SEQ ID NOS. 1–5. The components is administered in conjunction with an established drug treatment regimen such as DOTS. The administration of such components serves to revive dormant bacilli in the patient, making them susceptible to eradication by drug therapy. Otherwise, only non-dormant bacilli are eliminated and the patient is at risk for relapsing due to revival of the dormant bacilli after the treatment regimen has ceased. A combination of the above (e.g. more than one phospholipid, more than one peptide, or a combination of lipids and peptides) may also be administered. The quantity of the component to be administered may vary from patient to patient, depending on factors such as weight, gender, age, and general health, etc. of the patient, and it best determined by a skilled practitioner such as a physician. Generally, however, when a phospholipid is administered, the dosage will be in about the micromolar range, and when a protein or peptide is administered, the dosage will be in about the micromolar range.

Administration may be effected by any of a variety of routes that are well-known to those of skill in the art, including but not limited to oral, parenteral, intravenous, via inhalation, and the like.

To that end, the invention also provides a pharmacological preparation comprising cell extract or at least one substantially purified product of *M. tuberculosis* complex, the product displaying the property of resuscitating dormant bacilli of mycobacteria, or generally enhancing the growth of mycobacterium. The component may be a phospholipid or a component of a phospholipid, or a protein or fragment of the protein. In a preferred embodiment of the present invention, the phospholipid or component of a phospholipid is, for example, phosphotidyl-L-serine, dioleoyl phosphotidyl-L-serine, phosphotidylcholine, phosphotidylethanolamine, tuberculostearic acid, arachidonic acid, or a fatty acid. In another embodiment, the component is the protein Rv1147c or a peptide fragment of protein Rv1147c. Exemplary peptide fragments of Rv1147c include the peptides corresponding to SEQ ID NOS. 1–5. The pharmalogical preparation may also comprise a combination of the above (e.g. more than one phospholipid, more than one peptide, or a combination of lipids and peptides. Such a pharmacological preparation may also comprise other suitable substances and excipients, including but not limited to physiological acceptable buffering agents, stabilizers (e.g. antioxidants), flavoring agents, and the like. Further, the pharmacological preparation may be in any of a variety of art-accepted forms such as tablets, capsules, various injectable formulations, and the like, as are suitable for the desired means of administration.

In yet another aspect, the present invention provides a method of inhibiting the growth of a mycobacterium species such as *Mycobacterium tuberculosis, Mycobacterium paratuberculosis*, or *Mycobacterium leprae*. The method involves exposing the mycobacterium species to the isolated and sterilized supernatant of a culture *M. tuberculosis* complex or a cell extract of *M. tuberculosis* complex that is at least about 3 months in age. Alternatively, the method involves exposure of the mycobacterium species to substantially purified products from such a culture, wherein the products exhibit the property of inhibiting the growth of the mycobacterium species.

EXAMPLES

Methods

Bacterial Culture Conditions

*M. tuberculosis* H37Ra cultures were grown in 7H9 medium containing Tween 80 (0.05%) and ADC (albumin-dextrose-catalase) enrichment at 37° C. for various periods of time as standing batch cultures. Cultures of varying age up to one year were used for the resuscitation experiments. Resuscitation of dormant *M. tuberculosis* by phosphatidylserine was performed as follows. A 6 month old *M. tuberculosis* H37Ra culture was washed and resuspended in 7H9 medium followed by plating at different dilutions on 7H11 agar plates containing 4 μg/ml phosphatidylserine (derived from bovine brain, containing a mixture of two unknown fatty acyl groups, Sigma Chemical Co.) or phosphatidylserine dioleoyl. The plates were incubated at 37° C. for 3 weeks when the CFU was determined. Data represent average of duplicate samples.

Purification of Resuscitation Activity.

Spent culture supernatant from a 4-week-old stationary phase *M. tuberculosis* H37Ra culture grown in Sauton's medium (4 liters) was collected by centrifugation at 8000 rpm for 15 minutes. The supernatant was then passed through a SepPak Aluminum N column (Waters, Inc), which was washed with hexane and eluted with methanol:chloroform (1:2). The eluted materials were dried with Rotavapor R-3000 (BUCHI) and the dried materials were dissolved in a small volume of methanol:chloroform (1:2) and further fractionated by preparative thin layer chromatography on silica gel G60 using solvent system (chloroform:acetone:methanol:acetic acid:water=10:4:2:2:1). The silica gel from TLC plate was divided into 10 fractions, which were eluted with methanol:chloroform (1:2), dried by SpeedVac and assayed for resuscitation activity on the 6 month old H37Ra bacilli by FDA-EB staining. Active TLC fractions were pooled and further fractionated by reverse phase high-performance liquid chromatography (HPLC) on a Spectraphysics instrument, using a narrow bore mixed bed C18 cation-exchange column (Alltech), and a gradient using the following buffers: Buffer A (0.1% TFA in water) and Buffer B (0.1% TFA in acetonitrile). The eluate was monitored at 214 nm and 280 nm. Sixty HPLC fractions were collected and assayed for resuscitation activity on a 6 month old H37Ra culture using fluoroscein diacetate (FDA)-ethidium bromide (EB) viability staining (4), where live cells stained green and dead or injured cells red.

Mass Spectroscopic Analysis.

The active fractions were analyzed by matrix assisted laser desorption/ionization (MALDI) using a Kompac 4 MALDI instrument from Kratos. Fractions were analyzed in both positive and negative ion mode, using an extraction voltage of 20 kV and a 337 nm nitrogen laser. All spectra were the average of 50 laser shots. The matrix used was a saturated solution of α-cyano-4-hydroxycinnamic acid in 50% ethanol.

Protein Sequencing and Peptide Synthesis.

Protein sequencing of fractions 43 and 44 was performed in the Procise™ Protein Sequencing System machine (Applied Biosystems) by Edman degradation method, at Synthesis & Sequencing Facility of Johns Hopkins University School of Medicine. Overlapping synthetic peptides that cover the 8,331 Dalton secreted polypeptide:

P1 (NH2-DPVDAVINTTCNYGQVVAALNATD-OH) (residues 29–52; SEQ ID NO. 1);

P2 (NH2-LNATDPGAAAQFNASPVAQSYLRN-OH) (residues 48–71; SEQ ID NO. 2);

P3 (NH2-LRNFLAAPPPQRAAMAAQLQAV-OH) (residues 69–90; SEQ ID NO. 3); and

P4 (NH2-AQLQAVPGAAQYIGLVESVAGSCNNY-OH) (residues 85–110; SEQ ID NO. 4);

were synthesized at Synthesis & Sequencing Facility of Johns Hopkins University School of Medicine. Synthesis of P1 peptide was unsuccessful due to extreme hydrophobicity. The synthetic peptides were purified by HPLC and were over 95% pure.

Example 1

The Resuscitation Phenomenon in *M. tuberculosis*

*M. tuberculosis* H37Ra was cultivated in 7H9 Tween 80 (0.05%) albumin-dextrose-catalase liquid medium (Difco) for various times, ranging from a few weeks to several months and sometimes up to 2–3 years as standing batch cultures at 37° C. with occasional agitation. The standing aged batch cultures settled to the bottom of culture tubes with no apparent surface growth. The early stationary phase culture supernatant (ESPSN) from a 3–4 week old *M. tuberculosis* H37Ra standing culture grown in 7H9 medium was collected following centrifugation at 6,000 g and sterilized by filtration through 0.22 μm filter. The sterilized ESPSN did not form colonies on 7H11 agar plate. Portions of bacterial cell pellets (about $10^{7-8}$ bacilli in 100 µl) prepared from an 8 month old standing H37Ra batch culture were resuspended in the same volume (100 µl) of its own aged culture supernatant (A), fresh 7H9 medium (B), and filtered ESPSN (C). Upon incubation at 37° C. for 3 days without shaking, CFU in A, B, and C was determined by plating appropriate dilutions of the cell suspensions on 7H11 agar plates followed by incubation for 4 weeks at 37° C. The data are presented in Table 1. The bacilli from the 8 month old aged culture gave almost 1000 fold less colonies in its own aged culture supernatant than in fresh medium. This suggests that aged culture supernatant contained growth inhibitory activity. On the other hand, the aged bacilli incubated in ESPSN produced about 20 fold more colonies than the fresh medium control (Table 1). This indicates that ESPSN allowed a population of nonculturable bacilli (injured or dormant bacilli) to form colonies which otherwise failed to do so in fresh medium. The above phenomenon has been reproduced many times with different batches of aged *M. tuberculosis* H37Ra cultures of varying age up to 2–3 years using the same ESPSN. The resuscitation or growth stimulation phenomenon was also found with the bacilli grown in Sauton's medium, indicating that the type of medium is not important for production of the resuscitation activity by tubercle bacilli.

TABLE 1

Resuscitation activity in the early phase culture supernatant

| Treatment in various media | 8 month old *tubercle bacilli** plating efficiency (cfu/ml) |
|---|---|
| (A) own culture media | $2.0 \times 10^3$ |
| (B) 7H9 medium control | $1.2 \times 10^6$ |
| (C) ESPSN | $2.4 \times 10^7$ |

*The direct total count of the 8 month old culture was about $10^9$ bacilli/ml. The cfu counts were derived from the average of triplicate samples for appropriate dilutions on 7H11 agar plates

Example 2

Monitoring the Resuscitation Phenomenon by Fluoroscein Diacetate-Ethidium Bromide (FDA-EB) Staining Because cfu determination is time-consuming (4–6 weeks), we used FDA-EB staining (Kvach and Veras, 1982) to more rapidly assess the viability status of aged *M. tuberculosis* cultures upon treatment with ESPSN. The principle of FDA-EB staining is as follows: FDA crosses the membranes of dead and live cells, hydrolyzed into free fluorescein by both types of cell, but the latter is retained only by live cells with intact membrane. On the other hand, EB only enters dead cells or cells with impaired membrane integrity and stains DNA. Green cells stained by FDA were considered live cells, orange-red cells stained by EB dead cells, and dual-stained cells injured or dormant cells (Kvach and Veras, 1982). Briefly, mycobacterial cultures (100 µl) were stained for about 20 minutes with 50 µl FDA-EB working solution containing FDA and EB at 2 µg/ml and 4 µg/ml diluted from stock solution of FDA (5 mg/ml in acetone) and EB (2 mg/ml in PBS) in PBS buffer. The stained mycobacteria were examined under a fluorescence microscope with FITC (fluorescein isothiocyanates) filter with excitation at 490 nm and emission at 525 nm. FDA-EB staining has been shown to correlate with the viability or cfu of mycobacteria (Kvach and Veras, 1982). Using the FDA/EB staining, we examined the resuscitation phenomenon by ESPSN on bacilli from aged H37Ra standing batch cultures grown in 7H9 medium of varying age ranging from 8–16 months. Bacilli (about $10^{8-9}$ cells/ml) from various aged cultures were incubated with ESPSN or control 7H9 medium in a volume of 100 µl at 37° C. for 2 days followed by FDA-EB staining and fluorescence microscopy. The viability of the bacilli was determined by calculating the average percentage of green cells over total number of cells observed for at least 5 views under the microscope. Five to 20 fold more green cells were found when the bacilli from various aged cultures were treated with ESPSN than with fresh medium control (Table 2). These results suggest that the bacilli became more viable after resuscitation with ESPSN and that FDA/EB staining is a quick way to monitor the resuscitation process. Culture supernatants from early stationary phase cultures of *M. smegmatis* or *E. coli* had no effect on resuscitation or growth stimulation of aged tubercle bacilli.

TABLE 2

Effect of resuscitation medium (ESPSN) on the resuscitation of *M. tuberculosis* cultures of varying age by FDA-EB staining

| | Percentage (%) of green (live) cells determined by FDA-EB staining | | |
|---|---|---|---|
| Culture Age | Direct staining | Fresh 7H9 medium control | ESPSN |
| 8 month | 1.6 | 9.4 | 49.8 |
| 10 month | 1.8 | 2.4 | 49.2 |
| 15 month | 0 (all orange-red) | 0.8 | 19.4 |
| 16 month | 0 (all orange-red) | 0 (all orange-red) | 11.2 |

Example 3

Expression and Localization of the Resuscitation Activity.

To determine the presence of resuscitation activity in relation to growth phase, portions of filter-sterilized culture supernatant (100 µl) taken at different growth stage of an H37Ra standing culture (up to 8 weeks at 37° C.) were assayed on about $10^{7-8}$ bacilli from the same 8 month old culture as described in Table 1 using the FDA-EB staining. The resuscitation activity was present mainly from early stationary phase (3–4 weeks old) onwards up to 2 months we examined. There was hardly any resuscitation activity in the log phase (1–2 weeks old) culture supernatant (data not shown). To determine where the resuscitation activity is located, the culture supernatant and bacterial lysate of a 3–4 week old *M. tuberculosis* H37Ra culture were prepared and assayed for resuscitation activity similarly. The lysate was reconstituted to the original volume of the culture using 7H9 medium and sterilized by filtration through a 0.22 µm filter before use. The lysate was found to have about 1/40th of the activity as compared with that in the supernatant, indicating that the resuscitation activity is mainly present in the culture supernatant and only a small amount of this activity is present in the cell.

Example 4

The ESPSN Allowed Smaller Bacterial Inocula to Start Culture Growth Than Fresh Medium To start an *M. tuberculosis* culture requires a relatively large inoculum, and a small inoculum often fails to initiate the growth of *M. tuberculosis* in liquid culture (Dubos and Davis, 1946). The reason behind this observation is unknown. We tested if the ESPSN could influence the size of bacterial inoculum required to initiate growth of tubercle bacilli in liquid culture. To do this, a 6 month old *M. tuberculosis* H37Ra batch culture that had been kept at 37° C. without shaking was 10 fold serially diluted (0.4 ml into 3.6 ml) into filter-sterilized ESPSN (prepared from a 4 week old H37Ra standing culture grown in Sauton's medium) and into a control Sauton's medium. The Sauton's medium contained detergent Triton WR1339 at 0.025% to reduce bacterial clumping. The various dilutions were incubated at 37° C. for 2 weeks when the visibility of bacterial growth and cfu were determined. ESPSN allowed smaller inocula ($10^{-3}$ to $10^{-4}$) to form visible growth in liquid subcultures which otherwise failed to give any visible growth in Sauton's medium alone (Table 3, Panel A). The growth stimulating or resuscitation effect was also reflected in the increased cfu over the medium control (Table 3, Panel B). Strikingly, no cfu was demonstrable for $10^{-3}$ to $10^{-5}$ dilutions in medium control when directly plated, whereas $10^4$ to $10^5$ cfu/ml were detected for the same dilutions in ESPSN. Neither ESPSN alone nor the $10^{-6}$ dilutions in ESPSN or fresh medium gave any bacterial growth in liquid culture or on agar plates.

The age of the culture where the spent culture supernatant is derived is important. Log phase culture supernatant of MTB (less than 2 week old) has little growth enhancing or resuscitation activity. Early stationary and stationary phase culture supernatant (from 3–4 weeks up to 2 months old) have significant growth enhancing or resuscitation activity for MTB. Old spent culture supernatant of MTB (e.g., 3–12 months old culture) has growth inhibitory effect or toxic effect on the growth of MTB.

TABLE 3

Growth stimulation of 6-month-old *M. tuberculosis* cultures by ESPSN with small bacterial inocula

| | Visible growth[a] | | CFU/ml[b] | |
|---|---|---|---|---|
| Dilution | Sauton's | ESPSN | Sauton's | ESPSN |
| $10^{-1}$ | + | + | $5 \times 10^6$ | $>10^7$ |
| $10^{-2}$ | + | + | $10^6$ | $10^7$ |
| $10^{-3}$ | − | + | ND | $3 \times 10^5$ |
| $10^{-4}$ | − | + | ND | $2 \times 10^5$ |
| $10^{-5}$ | − | − | ND | $3 \times 10^4$ |
| $10^{-6}$ | − | − | ND | ND |

[a]+ = visible growth; − = no visible growth
[b]Determined from 2-week-old subcultures which had been inoculated with various dilutions of the 6-month-old culture diluted and grown in Sauton's medium alone or in ESPSN. Data are the averages of the results from triplicate platings of undiluted and diluted ($10^{-2}$) samples on 7H11 agar plates. ND, no CFU detectable when directly plated on agar plates.

Example 5

Characterization of the Resuscitation Activity

To determine the properties of the resuscitation activity in response to physicochemical factors as well as the nature of activity, we subjected the ESPSN to various treatments followed by assaying the resuscitation activity using the FDA-EB viability staining and fluorescence microscopy. In all the following experiments, the same 8 month old culture as described in Table 1 and a positive control ESPSN were used.

(a) Effect of temperature: Heat treatment of ESPSN at 100° C. for 10 minutes had no effect on the resuscitation activity, indicating this resuscitation factor is heat stable. This experiments also rules out the possibility that any residual bacilli or filterable form of the bacilli in the filtered culture supernatant may have contributed to the increased number of bacilli upon resuscitation. In addition, repeated freeze (−70° C.)/thaw (37° C.) for 10–15 cycles and storage of the ESPSN at −70° C. for 12 months had no significant effect on the resuscitation activity (data not shown).

(b) Effect of acid and alkali. ESPSN was incubated with 1 N HCl or 1 N NaOH for 1 hour at room temperature followed by neutralization with the same molar concentration of alkali or acid and was tested for resuscitation activity. Acid treatment completely abolished the resuscitation activity and alkali also inhibited the activity but to a lesser extent.

(c) Effect of pH on resuscitation phenomenon. To determine the pH conditions that may affect the resuscitation phenomenon, we adjusted the pH of ESPSN to 4.5, 5.0, 5.5, 6.0, 6.5, and 7.0 and sterilized the medium by filtering through a 0.22 μm filter. The cell pellets from an 18 month old H37Ra culture (100 μl) were resuspended in the ESPSN adjusted with various pH values followed by incubation at 37° C. for 2 days and the effect of resuscitation was examined by FDA-EB staining. Fresh 7H9 liquid medium was also adjusted to the above same pH values and included as controls. The resuscitation occurred mainly at neutral pH but not at acid pH.

(d) Nature of the resuscitation activity. RNase T1, DNase I, Exonuclease III were added to ESPSN at 2000 u/ml, 100 u/ml, 150 u/ml, respectively. Following incubation at 37° C. for 90 minutes, the enzymes were inactivated by heating at 70° C. for 15 minutes. Proteinase K, pronase, and trypsin were added to ESPSN at 20 μg/ml, 250 μg/ml and 25 μg/ml, respectively, and the mixtures were incubated at 37° C. for 1 hour followed by heat inactivation at 100° C. for 10–15 minutes. These treatments did not affect the resuscitation activity, indicating that the resuscitation factor is unlikely to be a polypeptide or nucleic acid.

(e) Preliminary determination of the molecular weight of the resuscitation activity. Bio-Gel-P2 (Bio-Rad) which separates compounds with small molecular weight (exclusion limit 1,800 Dalton) was used. Before the ESPSN sample was loaded, a molecular weight standard (Thyroglobulin, 670 kD; Bovine gamma globulin, 158 kD, Chicken ovalbumin, 44 kD; Equine myoglobin, 17 kD; and Vitamin B 12, 1.375 kD) was run and a standard curve was established with standard molecular weight versus elution volumes. After the ESPSN sample was loaded, the column was eluted with 7H9 medium without ADC, and various fractions were filtered through a 0.22μ filter before being tested for resuscitation activity using FDA/EB staining. The resuscitation activity was found to be smaller than the Vitamin B12 standard, which is 1,375 Dalton. Consistent with this finding, we found that dialysis of ESPSN using dialysis tubing with molecular weight cutoff of 3,000 Dalton caused complete loss of the activity (data not shown).

Example 6

Identification of Phospholipids as Having Resuscitation Activity From Culture Supernatants To identify the active components responsible for the resuscitation activity, spent culture supernatant from a stationary phase *M. tuberculosis* H37Ra culture was subjected to concentration and fractionation. Sixty HPLC fractions were assayed for resuscitation activity on a 6-month-old H37Ra culture using fluorocein diacetate-ethidium bromide (FDA-EB) viability staining. Fractions 1–4, and 46 had killing activity as judged by more EB-stainable red cells than control. Fractions 8, 22 and 23 and fractions 43 and 44 had prominent resuscitation activity as judged by presence of more FDA-stainable green cells. Analysis of fraction 8 was unsuccessful. Matrix-assisted laser desorption/ionization (MALDI) mass spectra obtained for fractions 22 and 23 both had a major peak at m/z 782 and a second peak at m/z 621. Presuming that the peak at m/z 782 is the protonated molecular ion and the second peak a fragment, the difference of 141 mass units is characteristic of the loss of a phosphoethanolamine head group from a phosphatidylethanolamine molecule (Heller et al., 1988) with an isotopically averaged molecular mass of 781. The remaining mass of the diacyl glycerol moiety may be accounted for by two fatty acids comprised of 39 carbons and 4 double bonds (C39:4). A composition of a C19:0 (RI) and C20:4 (R2) would be consistent with the molecular and fragment masses observed, and could include tuberculostearic acid [$CH_3(CH_2)_7CH(CH_3)$—$(CH_2)_8COOH$] and arachidonic acid [$CH_3(CH_2)_3(CH_2CH=CH)_4$—$(CH_2)_3COOH$].

To confirm that a phospholipid was responsible for activity, we first tested commercially available phosphatidyl-L-serine and a dioleoyl phosphatidyl-L-serine, both of which are precursor of phosphatidylethanolamine and phosphatidylcholine, for resuscitation activity for the 6 month old *M. tuberculosis* H37Ra cells. Both compounds had significant resuscitation activity over medium control as judged by colony forming units (CFU) assay. Phosphatidyl-L-serine and a dioleoyl phosphatidyl-L-serine at 4 μg/ml gave $1.2 \times 10^7$, $2 \times 10^6$ CFU/ml, respectively, whereas the medium control produced $3 \times 10^4$ CFU/ml. Phospholipase A2 and phospholipase C abolished the resuscitation of these compounds, whereas phospholipase D did not affect the growth enhancing effect of the phosphatidylserine derivatives (data not shown). In addition, phosphatidylcholine and phosphatidylethanolamine also had similar resuscitation and growth enhancing activity for *M. tuberculosis* as phosphatidylserine or phosphatidyl-serine-dioleoyl. However, structural analog phosphatidylglycerol-oleoyl-palmitoyl did not have significant activity.

It is well known that to initiate growth of *M. tuberculosis* in liquid culture a large inoculum is required (Dubos and Davis, 1946). In a separate experiment involving a fresh 4-week-old *M. tuberculosis* H37Ra culture, the culture was serially diluted into Sauton's medium (1 ml) alone or into medium containing 5 μg/ml phosphatidylserine at $10^{-2}$, $10^{-3}$, $10^{-4}$, $10^{-5}$, $10^{-6}$, $10^{-7}$ dilutions. The cultures were incubated at 37° C. for 20 days when the visible growth was assessed and the cultures were plated on 7H11 plates, which were incubated at 37° C. for 3 weeks. Phosphatidyl-L-serine allowed small inocula ($10^{-7}$ dilution) to form visible growth and CFU on plates, whereas the control culture grew only at $10^{-5}$ dilution. Taken together, these data suggest that the phospholipids not only resuscitated old tubercle bacilli but also allowed small inocula to initiate growth in liquid culture.

Example 7

Identification of an 8 kD Protein (Rv1174c) as Having Resuscitation Activity

MALDI mass spectroscopic analysis of fractions 43 and 44 both revealed a single peak at m/z 8,332, corresponding to the protonated molecular ion of a peptide with a molecular mass of 8,331 Daltons having the resuscitation activity. N-terminal amino acid sequencing identified the following peptide sequence:

NH2-DPVDAVINTTCNYGQVVAALNATDPGAAAQ-OH (SEQ ID NO. 5).

Homology search revealed that the peptide was identical to amino acid residues 29–58 of a hypothetical protein Rv1147c with unknown function from the *M. tuberculosis* genome sequence database (Cole et al., 1998). The predicted molecular mass of Rv1174c is 10,881 Dalton, suggesting that the first 28 amino acids of Rv1174c represents a signal sequence that is removed when secreted into the culture supernatant, giving rise to the 8,331 Dalton peptide.

To confirm that the Rv1174c has resuscitation activity, we attempted to overexpress this protein in *E. coli*. However, the recombinant Rv1174c was poorly expressed in *E. coli*. Nevertheless, culture supernatant of the recombinant *E. coli* strain expressing Rv1174c had resuscitation activity compared with vector control (data not shown). To circumvent this problem and bearing in mind that protein signaling molecules are often subject to proteolytic cleavage for activity (Dunny and Leonard, 1997), we made synthetic peptides that cover the 8,331 Dalton polypeptide and assayed their growth enhancing and resuscitation activity. Peptides P2, P3, P4 were tested on both fresh *M. tuberculosis* cells (4 week old) and old cells of varying age up to one year. Significant growth enhancement or resuscitation activity was observed for both types of cells, especially for old cells. Peptides P2, P3, P4 had significant growth enhancing effect over the control on a 4 week old H37Ra culture as judged by CFU counts (Table 4). The growth enhancing effect was more apparent after 5-day incubation with the peptides. Peptide P4 appeared to be more active than P2 and P3 in growth stimulation. The growth enhancement effect of a mixture of the P2, P3, P4 was better than the individual peptides used singly (Table 4).

TABLE 4

Effect of Rv1174 peptides on growth of fresh *M. tuberculosis* cells (CFU values × $10^5$/ml)

| Days | P2 | P3 | P4 | P2 + P3 + P4 | ESPSN | 7H9 |
|---|---|---|---|---|---|---|
| 3 | 2.25 | 4.5 | 20 | 15 | 2.25 | 1.5 |
| 5 | 5 | 450 | 32.5 | 75 | 100 | 6.5 |
| 8 | 150 | 1500 | 750 | 2500 | 150 | 10 |
| 11 | 750 | 1500 | 2000 | 4250 | 750 | 35 |

Data represent average of duplicate samples.

The resuscitation activity of the peptides on a standing 7 months old H37Ra culture was then tested. The peptides produced 10 to over 100 fold more CFUs than the control without peptides, and again the mixture of the 3 peptides produced best result (Table 5, A). Results of MTT redox dye (10) and FDA-EB viability staining (Table 5, B and C) correlated with the CFU data.

TABLE 5

Effect of Rv1174 peptides on growth of a 7-month-old *M. tuberculosis* H37Ra

| Days | P2 | P3 | P4 | P2 + P3 + P4 | 7H9 |
|---|---|---|---|---|---|
| A. CFU data (× $10^5$ CFU/ml) | | | | | |
| 5 | 100 | 40 | 50 | 100 | 13 |
| 10 | 200 | 800 | 900 | 2750 | 20 |

TABLE 5-continued

Effect of Rv1174 peptides on growth of a 7-month-old *M. tuberculosis* H37Ra

| Days | P2 | P3 | P4 | P2 + P3 + P4 | 7H9 |
|---|---|---|---|---|---|
| B. MTT data (OD readings at 570 nm) | | | | | |
| 0 | 0.2609 | 0.3147 | 0.2248 | 0.2365 | 0.2485 |
| 5 | 0.6269 | 0.6219 | 0.6287 | 0.6049 | 0.4803 |
| 10 | 1.1567 | 1.1917 | 1.4131 | 1.63971 | 0.774 |
| C. FDA-EB viability staining (% of viable green cells) | | | | | |
| 0 | 1 | 2 | 1 | 1 | 2 |
| 5 | 2 | 4.5 | 11.5 | 10 | 2 |
| 10 | 27.5 | 42.5 | 50 | 67.5 | 12.5 |

This finding was surprising in view of the previous observation (see Example 5) that the resuscitation activity of the spent supernatant was unlikely to be a polypeptide, in view of its insensitivity to treatment with Proteinase K, pronase, and trypsin.

Example 9

Antibody Raised Against the 8 kd-Derived Peptides Neutralize the Resuscitation Activity The ability of antibody raised against the peptides to block the growth enhancing effect of the peptides was assessed. Indeed, rabbit polyclonal antiserum against P2, P3, P4 was found to antagonize the growth enhancement activity of the peptides, whereas pre-immunization control serum did not have this effect (Table 6).

TABLE 6

Blocking of growth enhancing effect of Rv1174 peptides by specific polyclonal antiserum. CFU data(CFU: × $10^5$/ml)

| P2 + pre | P2 + Ab | P3 + pre | P3 + Ab | P4 + pre | P4 + Ab | P2 + P3 + P4 + pre | P2 + P3 + P4 + Ab | 7H9 + pre | 7H9 |
|---|---|---|---|---|---|---|---|---|---|
| 102.5 | 35 | 65 | 32.5 | 192.5 | 85 | 210.5 | 145.5 | 62.5 | 45 |

Data is average of duplicate samples. Pre, pre-immunization control serum; Ab, polyclonal antiserum raised against a mixture of P2, P3, and P4.

Example 10

Resuscitation of Truly Dormant Tubercle Bacilli That Did Not Contain Any CFU on Plates The most dramatic effect of the peptides was seen on the resuscitation of dormant bacilli from a one-year-old culture that had been incubated at 37° C. and dried up due to long term incubation and evaporation. The old culture when incubated in 7H9 liquid medium or 7H9 medium plus rabbit serum for 27 days and plated failed to produce any colonies on 7H11 plates. The reason to use rabbit serum is to see if serum might facilitate the recovery of old dormant bacilli, however, serum alone had no effect on reviving dormant bacilli. Even after prolonged incubation at 37° C. for up to 2 months, the dormant bacilli incubated with 7H9 medium or 7H9 plus rabbit serum produced no colonies on the 7H11 plates. Remarkably, in the presence of the peptides P2, P3, P4, dormant bacilli from the old culture became resuscitated and formed plenty of colonies. The degree of resuscitation correlated with peptide concentrations, as seen by appearance of 235, 170 and 7.5×$10^5$ CFU/ml at 10, 5 and 1 µg/ml of the peptides, respectively. This is the first demonstration that dormant tubercle bacilli in cultures that do not form colonies at all on plates could be resuscitated after appropriate treatment in vitro.

Example 11

Resuscitation of Dormant TB Bacilli From Mouse Tissues by Spent Culture Supernatant of *M. tuberculosis*

Mouse spleen tissue samples (A, B, and C) derived from mice that had been treated with antituberculosis drugs isoniazid and a new rifamycin derivative rifalazil did not give CFU on mycobacterial 7H11 agar plates. A resuscitation experiment was set up as follows to determine if the mouse tissues contained any dormant *M. tuberculosis* bacteria that could be resuscitated with the spent culture supernatant derived from *M. tuberculosis*. Tissue samples A, B, and C were inoculated into both fresh 7H9-ADC liquid medium and spent culture supernatant (in 7H9-ADC) of *M. tuberculosis* H37Ra and incubated at 37° C. without shaking for 8 weeks. Samples A and B failed to grow in either 7H9 medium or the spent culture supernatant. Interestingly, sample C, which failed to grow in fresh 7H9 medium, gave growth in the spent culture supernatant. When the growth in sample C was plated on 7H11 plates, the growth showed typical features of *M. tuberculosis* and the identity of *M. tuberculosis* was confirmed by PCR sequencing of the pncA gene. This is the first demonstration of resuscitation of dormant bacilli from in vivo derived tissues that were ostensibly sterile due to treatment by TB drugs.

This example demonstrates that mammalian tissue that is ostensibly free of *M. tuberculosis* may contain dormant forms of the organism which are capable of resuscitation by culturing in *M. tuberculosis* ESPSN culture medium.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Cole, S. T., Eiglmeier, K., Parkhill, J., James, K. D., Thomson, N. R., Wheeler, P. R., Honore, N., Garnier, T., Churcher, C., Harris, D., Mungall, K., Basham, D., Brown, D., Chillingworth, T., Connor, R., Davies, R. M., Devlin, K., Duthoy, S., Feltwell, T., Fraser, A., Hamlin, N., Holroyd, S., Hornsby, T., Jagels, K., Lacroix, C., Maclean, J., Moule, S., Murphy, L., Oliver, K., Quail, M. A., Rajandream, M. A., Rutherford, K. M., Rutter, S., Seeger, K., Simon, S., Simmonds, M., Skelton, J., Squares, R., Squares, S., Stevens, K., Taylor, K., Whitehead, S., Woodward, J. R., Barrell, B. G. (2001) Massive gene decay in the leprosy bacillus. *Nature* 409, 1007–1011.

Cole, S. T. Brosch, R. Parkhill, J., Garnier, T., Churcher, C., Harris, D., Gordon, S. V., Eiglmeier, K., Gas, S. Barry 3rd, C. E., Tekaia, F., Badcock, K., Basham, D., Brown, D., Chillingworth, T., Connor, R., Davies, R., Devlin, K., Feltwell, T., Gentles, S., Hamlin, N., Holroyd, S., Hornsby, T., Jagels, K. and Barrell, B. G. (1998) Deciphering the biology of *Mycobacterium tuberculosis* from the complete genome sequence. *Nature* 393, 537–544.

Dubos, R. J., and Davis, B. D. (1946) Factors affecting the growth of tubercle bacilli in liquid media. *J. Exp. Med.* 83, 409–423.

Dunny, G. M., and Leonard, B. A. B. (1997) Cell-cell communication in gram-positive bacteria. *Ann. Rev. Microbiol.* 51, 527–564.

Heller D. N., Murphy C. M., Cotter R. J., Fenselau, C., and Uy, O. M. (1988) Constant neutral loss scanning for the characterization of bacterial phospholipids desorbed by fast atom bombardment. *Analyt Chem* 60, 2787–2791.

McCune, R. M., Feldman, F. M., Lambert, H. P., and McDermott, W. (1966) Microbial persistence. I. The capacity of tubercle bacilli to survive sterilization in mouse tissues. *J. Exp. Med.* 123, 445–468.

McKinney, J. D. Jacobs, W. R., and Bloom, B. R. Persisting problems in tuberculosis, in Emerging Infections, R. Krause, J. I. Gallin, A. S. Fauci, Eds (Academic Press, New York, 1998), pp. 51–146.

WHO Report on the Tuberculosis Epidemic. (2000) Global Tuberculosis Programme, World Health Organization, Geneva, Switzerland.

We claim:

1. A supplemented medium for culturing mycobacteria, comprising
    a cell extract from *Mycobacterium tuberculosis* complex or at least one substantially purified product from *Mycobacterium tuberculosis* complex, wherein said cell extract or said substantially purified product exhibits growth enhancement activity for said mycobacteria, initiation of growth for small inocula, or resuscitation activity for dormant mycobacterial bacilli, and
    a suitable culture medium.

2. The supplemented medium of claim 1, wherein said mycobacteria is selected from the group consisting of *Mycobacterium tuberculosis* complex, *Mycobacterium paratuberculosis*, and *Mycobacterium leprae*.

3. The supplemented medium of claim 1, wherein said substantially purified product is selected from the group consisting of a component of early-stationary-phase culture supernatant, a component of stationary phase supernatant, and a component of a cell extract.

4. The supplemented medium of claim 1 wherein said substantially purified product is a phospholipid or a component of a phospholipid.

5. The supplemented medium of claim 4, wherein said phospholipid or said component of a phospholipid is selected from the group consisting of phosphotidyl-L-serine, dioleoyl phosphotidyl-L-serine, phosphotidylcholine, phosphotidylethanolamine, tuberculostearic acid, arachidonic acid, and C18–C31 fatty acids with or without double bonds, and esters of C18–C31 fatty acids with or without double bonds.

6. The supplemented medium of claim 1, wherein said substantially purified product is a peptide selected from the group consisting of a peptide corresponding to SEQ ID NO. 2, a peptide corresponding to SEQ ID NO. 3, and a peptide corresponding to SEQ ID NO. 4.

7. The supplemented medium of claim 1 wherein said suitable culture medium is selected from the group consisting of 7H12B, 7H9, 7H10, 7H11, Sauton's medium, Dubos medium, egg-based medium, and Lowenstein-Jensen medium.

8. A method for reviving dormant bacilli of a mycobacterium species, comprising the step of
    exposing said dormant bacilli of said mycobacterium species to cell extract of *Mycobacterium tuberculosis* complex or at least one substantially purified product of *Mycobacterium tuberculosis* complex, wherein said cell extract or said substantially purified product exhibits growth enhancement and resuscitation activity for mycobacteria, and wherein said substantially purified product is present in sufficient quantity to effect revival of said dormant bacilli of said mycobacterium species.

9. The method of claim 8 wherein said mycobacterium species is selected from the group consisting of *Mycobacterium tuberculosis* complex, *Mycobacterium paratuberculosis*, and *Mycobacterium leprae*.

10. The method of claim 8, wherein said substantially purified product is selected from the group consisting of a component of early-stationary-phase culture supernatant, a component of stationary phase supernatant, and a component of a cell extract.

11. The method of claim 8 wherein said substantially purified product is a phospholipid or a component of a phospholipid.

12. The method of claim 11, wherein said phospholipid or said component of a phospholipid is selected from the group consisting of phosphotidyl-L-serine, dioleoyl phosphotidyl-L-serine, phosphotidylcholine, phosphotidylethanolamine, tuberculostearic acid, arachidonic acid, and C18–C31 fatty acids with or without double bonds, and esters of C18–C31 fatty acids with or without double bonds.

13. The method of claim 8, wherein said substantially purified product is a peptide selected from the group consisting of a peptide corresponding to SEQ ID NO. 2, a peptide corresponding to SEQ ID NO. 3, and a peptide corresponding to SEQ ID NO. 4.

14. A method for the diagnosis of infection caused by a mycobacterium species, comprising,
    combining a sample for which the presence or absence of said mycobacterium species is to be determined with medium supplemented with cell extract of *Mycobacterium tuberculosis* complex or at least one substantially purified product of *Mycobacterium tuberculosis* complex in a culture, wherein said cell extract or said substantially purified product exhibits growth enhancement and resuscitation activity for mycobacteria; and
    analyzing said culture for the presence of said mycobacterium species, wherein a finding of the presence of said mycobacterium species indicates a positive diagnosis for said infection.

15. The method of claim 14, wherein said mycobacterium species is selected from the group consisting of *Mycobacterium tuberculosis* complex, *Mycobacterium paratuberculosis*, and *Mycobacterium leprae*.

16. The method of claim 14, wherein said substantially purified product is selected from the group consisting of a component of early-stationary-phase culture supernatant, a component of stationary phase supernatant, and a component of a cell extract.

17. The method of claim 14 wherein said substantially purified product is a phospholipid or a component of a phospholipid.

18. The method of claim 17, wherein said phospholipid or said component of a phospholipid is selected from the group consisting of phosphotidyl-L-serine, dioleoyl phosphotidyl-L-serine, phosphotidylcholine, phosphotidylethanolamine, tuberculostearic acid, arachidonic acid, and C18–C31 fatty acids with or without double bonds, and esters of C18–C31 fatty acids with or without double bonds.

19. The method of claim 14, wherein said substantially purified product is a peptide selected from the group consisting of a peptide corresponding to SEQ ID NO. 2, a peptide corresponding to SEQ ID NO. 3, and a peptide corresponding to SEQ ID NO. 4.

20. A kit for the diagnosis of infection caused by a mycobacterium species, comprising
a sealed container of medium supplemented with cell extract of *Mycobacterium tuberculosis* complex or at least one substantially purified product of *Mycobacterium tuberculosis* complex, wherein said substantially purified product exhibits growth enhancement and resuscitation activity for mycobacteria, in a carrier fluid.

21. The kit of claim 20 wherein said mycobacterium species is selected from the group consisting of *Mycobacterium tuberculosis* complex, *Mycobacterium paratuberculosis*, and *Mycobacterium leprae*.

22. The kit of claim 20, wherein said substantially purified product is selected from the group consisting of a component of early-stationary-phase culture supernatant, a component of stationary phase supernatant, and a component of a cell extract.

23. The kit of claim 20 wherein said substantially purified product is a phospholipid or a component of a phospholipid.

24. The kit of claim 23, wherein said phospholipid or said component of a phospholipid is selected from the group consisting of phosphotidyl-L-serine, dioleoyl phosphotidyl-L-serine, phosphotidylcholine, phosphotidylethanolamine, tuberculostearic acid, arachidonic acid and C18–C31 fatty acids with or without double bonds, and esters of C18–C31 fatty acids with or without double bonds.

25. The kit of claim 20, wherein said substantially purified product is a peptide selected from the group consisting of a peptide corresponding to SEQ ID NO. 2, a peptide corresponding to SEQ ID NO. 3, and a peptide corresponding to SEQ ID NO. 4.

26. A pharmacological agent for the treatment of an infection caused by a mycobacterium species, comprising,
cell extract of *Mycobacterium tuberculosis* complex or at least one substantially purified product of *Mycobacterium tuberculosis* complex, wherein said substantially purified product exhibits growth enhancement and resuscitation activity for mycobacteria, and
a physiologically suitable carrier.

27. The pharmacological agent of claim 26 wherein said mycobacterium species is selected from the group consisting of *Mycobacterium tuberculosis* complex, *Mycobacterium paratuberculosis*, and *Mycobacterium leprae*.

28. The pharmacological agent of claim 26, wherein said substantially purified product is selected from the group consisting of a component of early-stationary-phase culture supernatant, a component of stationary phase supernatant, and a component of a cell extract.

29. The pharmacological agent of claim 26 wherein said substantially purified product is a phospholipid or a component of a phospholipid.

30. The pharmacological agent of claim 29, wherein said phospholipid or said component of a phospholipid is selected from the group consisting of phosphotidyl-L-serine, dioleoyl phosphotidyl-L-serine, phosphotidylcholine, phosphotidylethanolamine, tuberculostearic acid, arachidonic acid, and C18–C31 fatty acids with or without double bonds, and esters of C18–C31 fatty acids with or without double bonds.

31. The pharmacological agent of claim 26, wherein said substantially purified product is a peptide selected from the group consisting of a peptide corresponding to SEQ ID NO. 2, a peptide corresponding to SEQ ID NO. 3, and a peptide corresponding to SEQ ID NO. 4.

32. A culture medium for culturing a mycobacterium species, comprising
isolated early-stationary-phase or stationary phase supernatant of *Mycobacterium tuberculosis* complex.

33. The culture medium of claim 32 wherein said mycobacterium species is selected from the group consisting of *Mycobacterium tuberculosis* complex, *Mycobacterium paratuberculosis*, and *Mycobacterium leprae*.

34. The culture medium of claim 32 wherein said isolated early-stationary-phase or stationary phase supernatant is sterile.

35. The culture medium of claim 34 wherein said isolated early-stationary-phase supernatant is sterilized by filtration.

36. A method for reviving dormant bacilli of a mycobacterium species, comprising the step of
exposing said dormant bacilli of said mycobacterium species to isolated early-stationary-phase or stationary phase supernatant of *Mycobacterium tuberculosis* complex, wherein said step of exposing causes revival of said dormant bacilli.

37. The method of claim 36 wherein said mycobacterium species is selected from the group consisting of *Mycobacterium tuberculosis* complex, *Mycobacterium paratuberculosis*, and *Mycobacterium leprae*.

38. The method of claim 36 wherein said isolated early-stationary-phase supernatant is sterile.

39. The method of claim 38 wherein said isolated early-stationary-phase supernatant is sterilized by filtration.

40. A kit for the diagnosis of infection caused by a mycobacterium species, comprising
a sealed container comprising isolated early-stationary-phase or stationary phase supernatant from a culture of *Mycobacterium tuberculosis* complex.

41. The kit of claim 40 wherein said mycobacterium species is selected from the group consisting of *Mycobacterium tuberculosis* complex, *Mycobacterium paratuberculosis*, and *Mycobacterium leprae*.

42. The kit of claim 40 wherein said isolated early-stationary-phase or stationary phase supernatant is sterile.

43. The kit of claim 42 wherein said isolated early-stationary-phase or stationary phase supernatant is sterilized by filtration.

44. A method for the diagnosis of infection caused by a mycobacterium species comprising,
combining a sample for which the presence or absence of said mycobacterium species is to be determined with isolated early-stationary-phase or stationary phase supernatant of *Mycobacterium tuberculosis* complex in a culture; and analyzing said culture for the presence of said mycobacterium species, wherein a finding of the presence of said mycobacterium species indicates a positive diagnosis for said infection.

45. The method of claim 44 wherein said mycobacterium species is selected from the group consisting of *Mycobacterium tuberculosis* complex, *Mycobacterium paratuberculosis*, and *Mycobacterium leprae*.

46. The method of claim 44 wherein said isolated early-stationary-phase or stationary phase supernatant is sterile.

47. The method of claim 46 wherein said isolated early-stationary-phase or stationary phase supernatant is sterilized by filtration.

48. A method of inhibiting the growth of a species of mycobacterium comprising the step of exposing said mycobacterium an isolated supernatant or cell extract from a culture of *Mycobacterium tuberculosis* complex that is at least 3 months old, wherein said step of exposing has the effect of inhibiting the growth of said species of mycobacterium.

49. The method of claim 48 wherein said mycobacterium species is selected from the group consisting of *Mycobacterium tuberculosis* complex, *Mycobacterium paratuberculosis*, and *Mycobacterium leprae*.

50. The method of claim 48 wherein said isolated early-stationary-phase or stationary phase supernatant is sterile.

51. The method of claim 50 wherein said isolated early-stationary-phase or stationary phase supernatant is sterilized by filtration.

52. A method for enhancing the growth of a mycobacterium species, comprising, culturing said mycobacterium species in a culture medium supplemented with cell extract of *Mycobacterium tuberculosis* complex or at least one substantially purified product of *Mycobacterium tuberculosis* complex, wherein said cell extract or said substantially purified product exhibits growth enhancement for said mycobacterium species.

53. The method of claim 52, wherein said mycobacterium species is selected from the group consisting of *Mycobacterium tuberculosis* complex, *Mycobacterium paratuberculosis*, and *Mycobacterium leprae*.

54. The method of claim 52, wherein said substantially purified product is selected from the group consisting of a component of early-stationary-phase culture supernatant, a component of stationary phase supernatant, and a component of a cell extract.

55. The method of claim 52 wherein said substantially purified product is a phospholipid or a component of a phospholipid.

56. The method of claim 55, wherein said phospholipid or said component of a phospholipid is selected from the group consisting of phosphotidyl-L-serine, dioleoyl phosphotidyl-L-serine, phosphotidylcholine, phosphotidylethanolamine, tuberculostearic acid, arachidonic acid, and C18–C31 fatty acids with or without double bonds, and esters of C18–C31 fatty acids with or without double bonds.

57. The method of claim 52 wherein said substantially purified product is a peptide is selected from the group consisting of a peptide corresponding to SEQ ID NO. 2, a peptide corresponding to SEQ ID NO. 3, and a peptide corresponding to SEQ ID NO. 4.

* * * * *

SEQUENCE LISTING

```
<160> NUMBER OF SEQ ID NOS: 5

<210> SEQ ID NO 1
<211> LENGTH: 24
<212> TYPE: PRT
<213> ORGANISM: Mycobacterium tuberculosis

<400> SEQUENCE: 1

Asp Pro Val Asp Ala Val Ile Asn Thr Thr Cys Asn Tyr Gly Gln Val
1               5                   10                  15

Val Ala Ala Leu Asn Ala Thr Asp
            20

<210> SEQ ID NO 2
<211> LENGTH: 24
<212> TYPE: PRT
<213> ORGANISM: Mycobacterium tuberculosis

<400> SEQUENCE: 2

Leu Asn Ala Thr Asp Pro Gly Ala Ala Ala Gln Phe Asn Ala Ser Pro
1               5                   10                  15

Val Ala Gln Ser Tyr Leu Arg Asn
            20

<210> SEQ ID NO 3
<211> LENGTH: 22
<212> TYPE: PRT
<213> ORGANISM: Mycobacterium tuberculosis

<400> SEQUENCE: 3

Leu Arg Asn Phe Leu Ala Ala Pro Pro Pro Gln Arg Ala Ala Met Ala
1               5                   10                  15

Ala Gln Leu Gln Ala Val
            20

<210> SEQ ID NO 4
<211> LENGTH: 26
<212> TYPE: PRT
<213> ORGANISM: Mycobacterium tuberculosis
```

-continued

```
<400> SEQUENCE: 4

Ala Gln Leu Gln Ala Val Pro Gly Ala Ala Gln Tyr Ile Gly Leu Val
1               5                   10                  15

Glu Ser Val Ala Gly Ser Cys Asn Asn Tyr
            20                  25

<210> SEQ ID NO 5
<211> LENGTH: 30
<212> TYPE: PRT
<213> ORGANISM: Mycobacterium tuberculosis

<400> SEQUENCE: 5

Asp Pro Val Asp Ala Val Ile Asn Thr Thr Cys Asn Tyr Gly Gln Val
1               5                   10                  15

Val Ala Ala Leu Asn Ala Thr Asp Pro Gly Ala Ala Ala Gln
            20                  25                  30
```